United States Patent
Carinci et al.

(10) Patent No.: US 10,823,803 B2
(45) Date of Patent: Nov. 3, 2020

(54) METHOD AND APPARATUS FOR RECONSTRUCTING CONTRAST LEVELS FROM MAGNETIC RESONANCE ACQUISITIONS

(71) Applicant: Siemens Healthcare GmbH, Erlangen (DE)

(72) Inventors: Flavio Carinci, Wuerenlingen (CH); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/383,867

(22) Filed: Apr. 15, 2019

(65) Prior Publication Data
US 2019/0317169 A1 Oct. 17, 2019

(30) Foreign Application Priority Data
Apr. 16, 2018 (EP) .................................. 18167497

(51) Int. Cl.
*G01R 33/561* (2006.01)
*A61B 5/055* (2006.01)
(Continued)

(52) U.S. Cl.
CPC .......... *G01R 33/5611* (2013.01); *A61B 5/055* (2013.01); *G01R 33/4818* (2013.01);
(Continued)

(58) Field of Classification Search
CPC .. G01R 33/5611; G01R 33/543; G01R 33/50; G01R 33/4818; G01R 33/5608;
(Continued)

(56) References Cited

U.S. PATENT DOCUMENTS 7,432,707 B1 * 10/2008 Boitano ................ G01R 33/56
324/309
2006/0233455 A1 * 10/2006 Cheng .............. G01R 33/56563
382/274
(Continued)

FOREIGN PATENT DOCUMENTS

DE 102016219052 B3 3/2018

OTHER PUBLICATIONS

Marques et al.: "MP2RAGE, a self bias-field corrected sequence for improved segmention and T1-mapping at high field"; Neuroimage 49, 1271 (2010), journal homepage: www.elsevier.com/locate/ynimg, pp. 1271-1281; 2009.
(Continued)

*Primary Examiner* — G. M. A Hyder
(74) *Attorney, Agent, or Firm* — Schiff Hardin LLP

(57) ABSTRACT

In a method for reconstructing contrast levels from magnetic resonance (MR) acquisitions using a parallel acquisition (PAT) technique, MR raw data for at least two contrast levels are generated or acquired, the raw data includes reference lines. Reference line images are reconstructed from the reference lines of the MR raw data for at least two of the contrast levels. A histogram analysis is implemented on the basis of the reference line images. A PAT reconstruction of image representations of the different contrast levels is implemented, wherein the decision as to which reference lines are used for the PAT reconstruction being made on the basis of the histogram analysis.

11 Claims, 6 Drawing Sheets

(51) Int. Cl.
*G01R 33/48* (2006.01)
*G01R 33/50* (2006.01)
*G01R 33/54* (2006.01)
G01R 33/36 (2006.01)
G01R 33/385 (2006.01)
G01R 33/56 (2006.01)

(52) U.S. Cl.
CPC ........... *G01R 33/50* (2013.01); *G01R 33/543* (2013.01); *G01R 33/36* (2013.01); *G01R 33/385* (2013.01); *G01R 33/5601* (2013.01); *G01R 33/5608* (2013.01)

(58) Field of Classification Search
CPC .. G01R 33/5601; G01R 33/385; G01R 33/36; A61B 5/055
See application file for complete search history.

(56) References Cited

U.S. PATENT DOCUMENTS

| | | |
|---|---|---|
| 2009/0224756 A1 | 9/2009 | Machida et al. |
| 2014/0376794 A1 | 12/2014 | Dumoulin et al. |
| 2018/0095143 A1 | 4/2018 | Zeller |

OTHER PUBLICATIONS

Griswold, Mark A. et al. "Generalized Autocalibrating Partially Parallel Acquisitions (GRAPPA)"; in: Magnetic Resonance in Medicine; vol. 47; pp. 1202-1210; 2002.

* cited by examiner

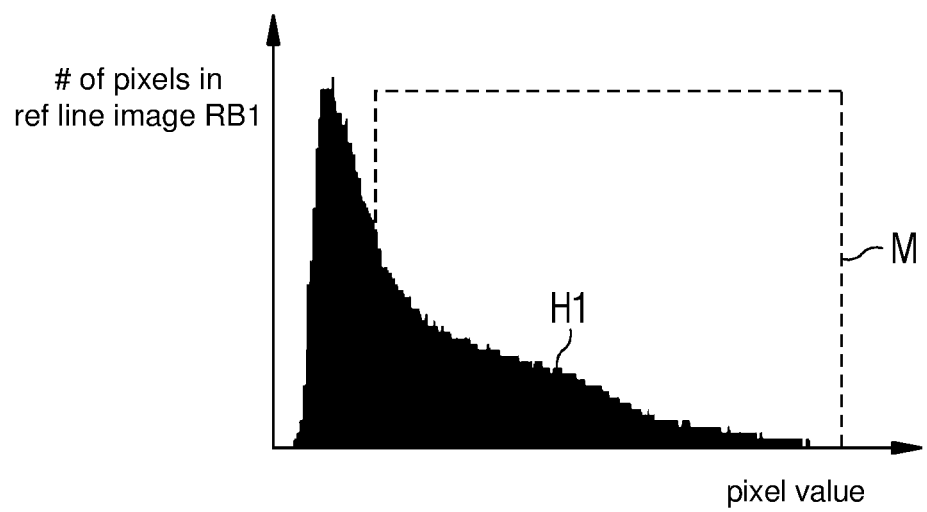
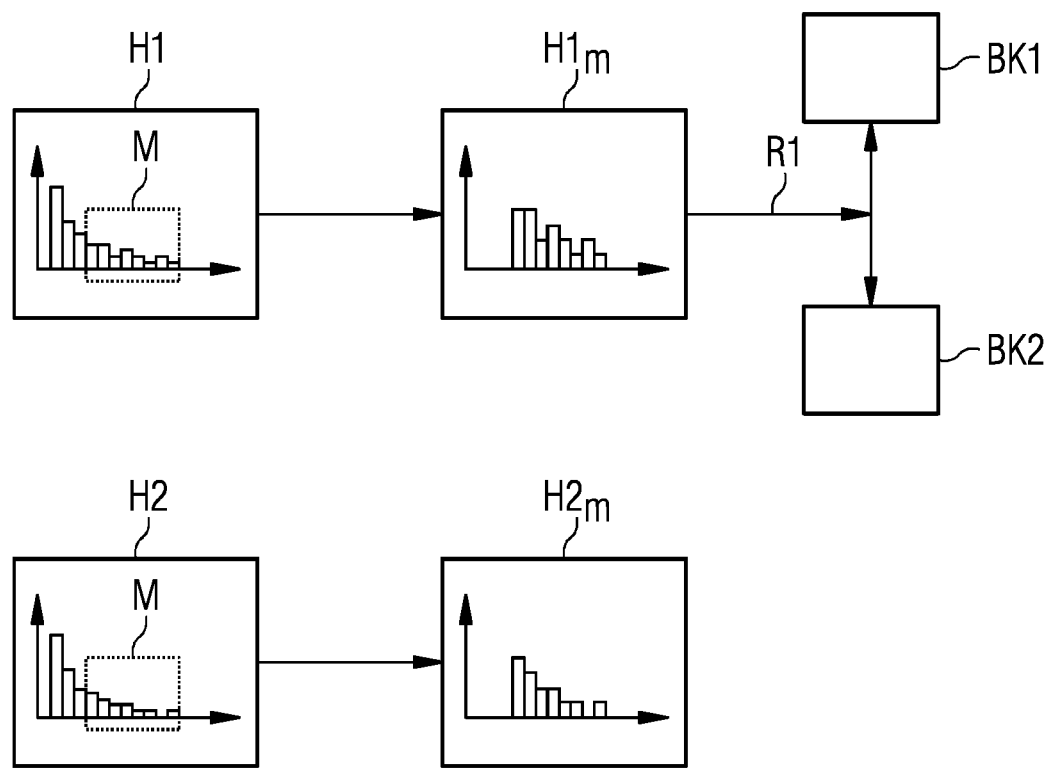

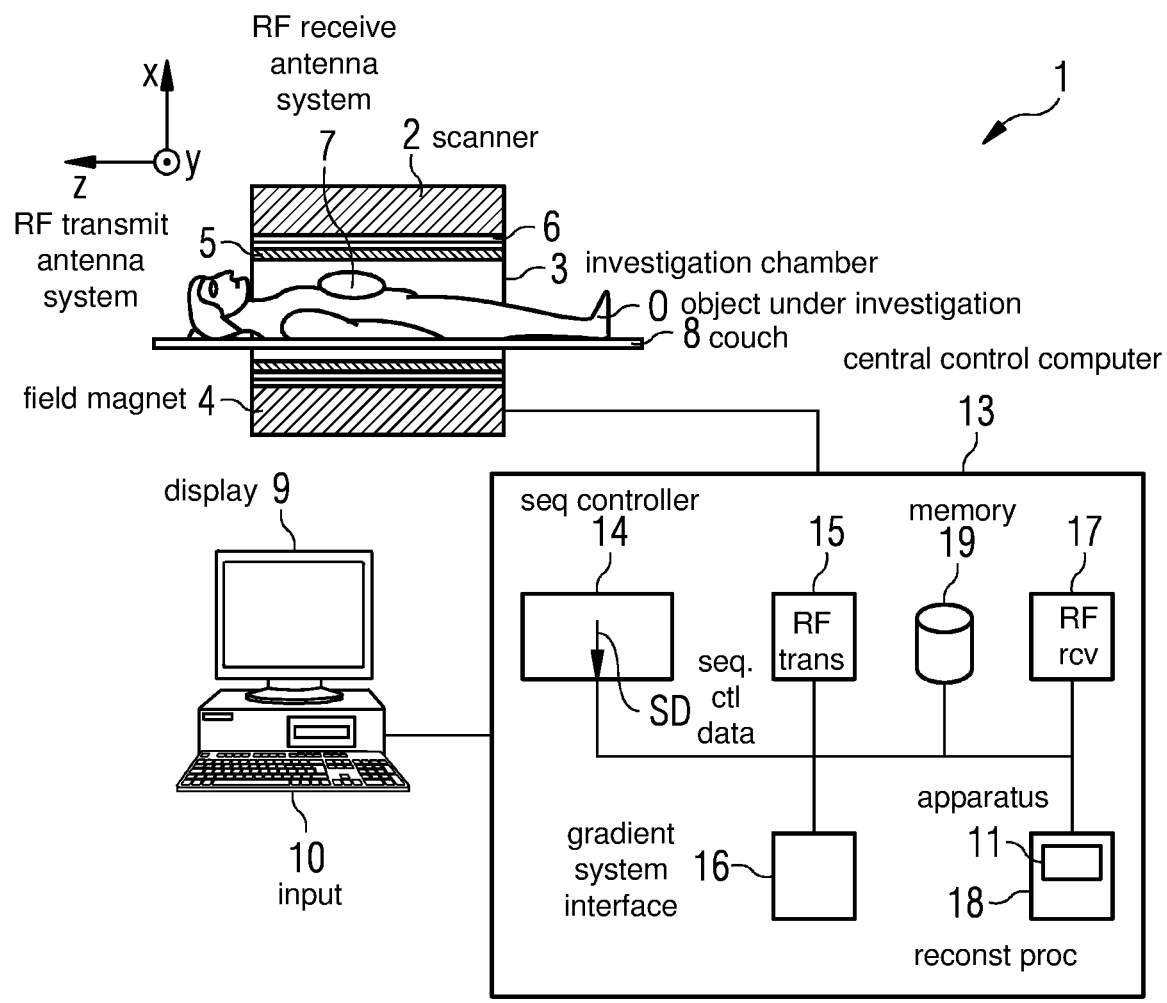

METHOD AND APPARATUS FOR RECONSTRUCTING CONTRAST LEVELS FROM MAGNETIC RESONANCE ACQUISITIONS

BACKGROUND OF THE INVENTION

Field of the Invention

The invention concerns a method and an apparatus for reconstructing contrast levels from magnetic resonance acquisitions by the use of a parallel acquisition technique ("PAT"), as well as a corresponding magnetic resonance tomography apparatus and a non-transitory data storage medium.

Description of the Prior Art

In a magnetic resonance scanner, the body to be examined is conventionally exposed to a relatively strong basic magnetic field, for example of 1.5 tesla, 3 tesla or 7 tesla, with the use of a basic field magnet. Once the basic field has been applied, nuclei in the object under investigation align themselves so as to have a non-vanishing nuclear magnetic dipole moment, frequently also denoted spin, along the basic field. This collective behavior of the spin system is described macroscopically as "magnetization". Macroscopic magnetization is the vector sum of all the microscopic magnetic moments in the object at a specific location. In addition to the basic field, a magnetic field gradient is applied with the use of a gradient system, the gradient determining the magnetic resonance frequency (Larmor frequency) at the respective location. Radio-frequency excitation signals (RF pulses) are then emitted via a radio-frequency transmit system by means of suitable antenna devices, which is intended to result in the nuclear spins of specific nuclei resonantly excited by this radio-frequency field (i.e. at the Larmor frequency present at the respective location) being tilted by a defined flip angle relative to the magnetic field lines of the main magnetic field. If such an RF pulse acts on spins that are already excited, the latter can be tilted into another angular position or even flipped back into in an initial state parallel to the basic magnetic field. On relaxation of the excited nuclear spins, radio-frequency signals, or "magnetic resonance signals", are emitted and are received by suitable receiving antennas (also denoted magnetic resonance coils or reception coils), then demodulated and digitized and then further processed as raw data. The magnetic resonance signals are acquired in the spatial-frequency domain, or k-space. During a measurement (data acquisition), for example of a slice of the subject of the filing (also called "scanner") of k-space, with acquired data proceeds over time along a gradient trajectory (also denoted k-space trajectory) defined by switching of the gradient pulses. The RF pulses must be emitted in temporally coordinated manner. After further processing steps, which are generally also dependent on the acquisition method, the desired image data are finally reconstructed by a two-dimensional Fourier transformation of the raw data acquired in this manner. Alternatively, three-dimensional volumes can also be excited and read out in a defined manner. After further processing steps, the 3D raw data form a three-dimensional k-space. A three-dimensional image data volume may then correspondingly be reconstructed by a three-dimensional Fourier transformation.

During measurement, a magnetic resonance tomography scanner is conventionally operated using specific predetermined pulse sequences, i.e. sequences of defined RF pulses, gradient pulses in various directions, and read-out windows, during which the receiving antennas are switched to a reception mode and the magnetic resonance signals are received and processed. Using a measurement protocol, these sequences are preconfigured for a desired investigation, for example a specific contrast level of the calculated images. The measurement protocol may also contain further control data for the measurement. There are numerous magnetic resonance sequencing techniques that can be used for constructing pulse sequences. One of the major challenges facing the future development of magnetic resonance imaging (MR imaging) is how to accelerate magnetic resonance sequencing techniques without extensive compromises in terms of resolution, contrast level and susceptibility to artifacts.

At present, clinical MR imaging is almost exclusively based on Cartesian or rectilinear imaging, in which the sampled k-space points (i.e. the points in k-space at which raw data are entered) are located at the lattice points of a rectilinear lattice or grid. The use of parallel imaging methods has made it possible to accelerate clinical MR imaging significantly. In parallel MR imaging (PAT), data acquisition is shortened by some of the lines in k-space grid which are actually necessary for reconstructing an aliasing-free image not being filled with data. These missing lines are subsequently replaced in k-space during image reconstruction or the aliasing artifacts in the image space that arise from this undersampling are removed. One prerequisite for being able to use parallel imaging methods is receiving the MR signal with a number of reception coils (antennas), and the spatial sensitivity (reception profile) of the individual reception coils must be known. The spatial sensitivity of the reception coils is calculated with the use of coil calibration data. The coil calibration data generally must be adequately sampled. Since sensitivities generally undergo slow spatial variation, it is generally sufficient for the coil calibration data to be of low spatial resolution. In general, coil calibration data must be remeasured for each patient. One of the most important parallel imaging methods is the "GRAPPA" method, as described for example in the paper "Generalized Autocalibrating Partially Parallel Acquisitions (GRAPPA)" by Marc Griswold et al. in Magnetic Resonance in Medicine 47, 2002, pages 1202 to 1210. The "missing" raw data $s_i(k_y,k_x)$ of coil i at k-space position $k=(k_y,k_x)$ with k-space coordinates (ky,kx) at which no data was acquired is here calculated or interpolated as a linear combination of all measured data points in a specified surrounding area or vicinity $\Omega(k_y,k_z)$ of the missing sampling point:

$$s_i(k_y, k_x) = \sum_{j=1}^{N_c} \sum_{(q_y,q_x) \in \Omega_{(ky,kx)}} n_{i,(k_y,k_x)}(j, q_y, q_x) s_j(q_y, q_x) \quad (1)$$

wherein i and j are the control variables for the individual reception coils used in the parallel measurement and in each case run from 1 to NC, the maximum number of reception coils used. The outer (first) sum in equation (1) includes all the reception coils and the inner (second) sum includes all the "measured" sampling points at which raw data was acquired and which fall within a defined vicinity $\Omega(k_y,k_z)$ of each "missing" sampling point with k-space coordinates $(k_y,k_x)$. $s_j(q_y,q_x)$ is in each case the signal measured by the jth receive coil at the sampling point with k-space coordinates $(q_y,q_x)$ (i.e. the raw data acquired there). $n_i$, $(k_y,k_x)$ are the complex linear factors which weight the individual measured data points in the surrounding areas $\Omega(k_y,k_x)$ and are initially unknown. The index $\{i, (k_y,k_x)\}$ here indicates that, in general, a separate set of linear factors is required not only for each coil i but also for each unmeasured data point with the coordinates $(k_y,k_x)$.)

One central point of this method is that the coefficients or weighting factors $n_i$, $(k_y,k_x)$ (hereinafter also denoted "GRAPPA weights") in formula (1) for rectilinear imaging are independent of the location $(k_y,k_x)$ of the sampling point in the grid but are instead solely dependent on the spacing between the respective neighboring sampling points which are taken into account:

$$s_i(k_y, k_x) = \sum_{j=1}^{N_C} \sum_{l=0}^{N_y-1} \sum_{m=0}^{N_x-1} n_i(j, l, m) s_j \left( k_y + (Al - l_0)\Delta k_y, k_x + \left(m - \frac{N_x}{2}\right) \Delta k_x \right) \quad (2)$$

wherein $\Delta k_y$ is the lattice spacing (grid pitch) between adjacent sampling points in the phase-encoding direction, $\Delta k_x$ is the lattice spacing between adjacent sampling points in the frequency-encoding direction and A is the acceleration factor. l and m are control variables of the neighboring sampling points. $I_0$ is selected such that all the sampling points on the right-hand side of the equation (2) were measured and are neighboring sampling points of $s_i$. $n_i$ are in turn the complex linear factors which weight the individual measured data points in the surrounding area and are initially unknown. In equation (2), the rectilinear surrounding area of each unmeasured data point comprises $N_x \times N_y$ measured data points, each one of which was acquired with $N_c$ different component coils. Since on the left side of equation (2) the unmeasured data are separately calculated for each component coil and the linear factors differ for different component coils, overall $N_{unknown} = N_c \cdot N_y \cdot N_x \cdot N_C$ complex GRAPPA weights are required in order to be able to reconstruct the unmeasured data. The GRAPPA weights are obtained by measuring a second data set known as the coil calibration data set. This coil calibration data set is sampled or measured completely (thus sufficiently according to Nyquist). Due to the complete sampling, both the raw data $s_i(k_y,k_x)$ on the left side of equation (2) and the raw data $s_i(q_y,q_x)$ on the right side of equation (2) are known for the second data set. If the coil calibration data set is composed of at least as many data points as there are unknown GRAPPA weights, the GRAPPA weights can be calculated. Equation (2) thus can most simply be written in matrix form for each component coil:

$$s_i = G \cdot n_i \quad (3)$$

wherein $n_i$ is here a column vector of length $N_y \cdot N_x \cdot N_C$, the components of which contain the sought GRAPPA weights for coil i. Column vector $s_i$ is a vector consisting of M data points of the coil calibration data set for which all the neighbors in the selected rectilinear surrounding area have also been measured. Column vector $s_i$ thus has length M and contains only data points from the selected component coil i. G is accordingly an $M \times N_y \cdot N_x \cdot N_C$ matrix. The elements of matrix G consist of measured data points. The $m^{th}$ line of the matrix G thus consists of the total $N_y \cdot N_x \cdot N_C$ data points in the rectilinear surrounding area of the $m^{th}$ data point according to equation (3).

In general, so many sampling points are measured that the equation system is overdetermined. This equation system is then solved using standard methods on the basis of the smallest square deviation.

In summary, an acquisition technique that is frequently used for the purposes of magnetic resonance tomography involves acquiring a number of acquisitions with a different contrast level and subsequently combining or appropriately post-processing them. These include, for example, acquisition techniques known as MapIT ("MAgnetic Particle Imaging Technology"), DIXON, Diffusion, MP2RAGE ("Magnetization Prepared Two RApid Gradient Echo").

One drawback of the prior art is that using GRAPPA for reducing acquisition time results in disadvantageous image quality which may go as far as distinct artifacts. This is because, in order to minimize the image reconstruction time, GRAPPA weights are only calculated for one of the various contrast levels which are acquired. These GRAPPA weights are, however, then used for reconstructing all the contrast levels.

For example, the MP2RAGE acquisition technique involves acquiring two different IR contrast levels with different inversion times TI, wherein, after an inversion pulse (IR pulse), two subsequent IR contrast levels are acquired. The reference lines required for PAT are taken from the first contrast level. Since in this case (i.e. for this TI), the first contrast level turns out to be distinctly darker and lower (low signal-noise ratio due to selected inversion time), the reference lines used are non-optimal for PAT reconstruction of the second contrast level. If the reference lines from the second contrast level are selected for image reconstruction, depending on the TI times selected, this may be suboptimal for the first contrast level. Separately acquiring the reference lines for the two contrast levels is suboptimal timewise and may likewise provide fluctuating signal-noise ratios for the two contrast levels.

In addition to Cartesian imaging, interest has recently also been growing in the use of radial scanning of k-space, primarily because of its relative insensitivity to movement. In such radial scanning, data are acquired along radial spokes that each pass through k-space center. The relative insensitivity to movement is due to the repeated acquisition of the central k-space region. However, the previously described disadvantages also occur in the above-stated acquisition technique.

SUMMARY OF THE INVENTION

An object of the present invention is to provide an alternative, more convenient method and an apparatus for reconstructing contrast levels from magnetic resonance acquisitions using a parallel acquisition technique, and a corresponding control computer and a corresponding magnetic resonance tomography apparatus, with which the above-described disadvantages are avoided.

The method according to the invention serves to reconstruct contrast levels from magnetic resonance acquisitions using a parallel acquisition technique ("PAT") or an integrated parallel acquisition technique ("iPAT") in order to improve image quality in multi-contrast level acquisitions.

The method according to the invention starts with the step of providing magnetic resonance raw data to a computer, or generating magnetic resonance raw data by operating a magnetic resonance scanner. The magnetic resonance raw data are acquired by a magnetic resonance tomography (MRT) scanner, or are data that have previously been acquired.

The magnetic resonance raw data contain information regarding at least two contrast levels and include reference lines. The magnetic resonance raw data thus contain reference lines about the contrast levels, i.e. for at least two of these contrast levels. It should be noted that the magnetic resonance raw data may only include data from which the images of the contrast levels are subsequently reconstructed ("primary data"), wherein the reference lines are present therein. In addition to the main data, the magnetic resonance raw data may also include further specific reference data about reference lines regarding the acquired contrast levels.

Reference lines are regions in k-space that are used for calculating the GRAPPA kernel, or in SENSE for determining coil sensitivities. This is generally a small, central portion of k-space. Typical sizes are 20 to 30 reference lines. The reference lines may be radial lines or rectilinear lines.

One example of a suitable acquisition sequence is the MP2RAGE sequence, which provides data at two different contrast levels.

The inventive method then proceeds with the step of reconstructing reference line images. These reference line images are typically generated with a comparatively low resolution in order to ensure a rapid procedure. Reconstruction proceeds from a set of reference lines of the magnetic resonance raw data for at least two of the contrast levels.

Consistent with the above-stated examples regarding the nature of the magnetic resonance raw data, it is possible to use the primary data regarding the contrast levels or the reference data, for reconstructing the reference line images.

A PAT reconstruction is not necessarily required for reconstruction of reference line images. It is advantageous to use a reconstruction method that can be carried out quickly for this purpose.

In a further step of the inventive method, a histogram analysis takes place, wherein the reference line images are analyzed on the basis of histograms. Analysis is carried out such that a decision can be made as to which reference lines are to be used for a PAT reconstruction.

The inventive method then proceeds with a PAT reconstruction. The PAT reconstruction of image representations of the different contrast levels is carried out using the reference lines for the PAT reconstruction that were determined by the histogram analysis.

An apparatus according to the invention for reconstructing contrast levels from magnetic resonance acquisitions with a parallel acquisition technique has the following components.

A data interface receives or acquires magnetic resonance raw data for at least two contrast levels, wherein the magnetic resonance raw data includes reference lines.

A reference line image reconstruction processor is designed for automatic reconstruction of reference line images from the reference lines of the magnetic resonance raw data, for at least two of the contrast levels.

An analysis processor is designed for histogram analysis of the reference line images.

An image reconstruction processor is designed for PAT reconstruction of image representations of the different contrast levels, wherein the decision as to which reference lines are used for the PAT reconstruction is made on the basis of the histogram analysis.

A control computer according to the invention controls a magnetic resonance tomography scanner so as to implement the method according to the invention.

A magnetic resonance tomography apparatus according to the invention has a scanner that is operated by the control computer according to the invention.

A major part of the above-stated components of the apparatus or control device can be realized entirely or in part in the form of software modules in a processor of a corresponding apparatus or control device. A largely software-based realization has the advantage that apparatuses or control devices which are already in service can also straightforwardly be retrofitted to operate in the manner according to the invention by means of a software update.

Accordingly, the present invention also encompasses a non-transitory, computer-readable data storage medium encoded with programming instructions that, when the storage medium is loaded into a stand-alone computer, or a computer or a computer system of a magnetic resonance apparatus, cause the stand-alone computer or the computer or the computer system to implement any or all embodiments of the method according to the invention, as described above.

Individual features of different exemplary embodiments or variants may be combined to form new exemplary embodiments or variants.

For the purpose of the histogram analysis, an individual histogram for each reference line image is preferably calculated in each case for at least two, in particular for all, reference line images. The decision as to which reference lines are used for PAT reconstruction is then preferably made on the basis of the signal strength of the pixels, classified in the histogram, of these reference line images. The reference lines selected are here preferably those for which the pixels thereof that are classified in the histogram, have the highest signal strength. The centroid of the distribution plotted in the histogram is preferably considered, rather than merely those pixels that exhibit the highest signal strength.

The mean deviation and the standard deviation of the signal distribution in the reference line images, in particular in the histograms thereof, are preferably determined in the histogram analysis.

After reconstruction of the reference line images and before histogram analysis, the reference line images and/or the histograms thereof are preferably masked by a mask. For example, the number of pixels within the mask is determined from a masked image or only those pixels which are within the mask are included in a histogram. A reference line image and/or a histogram may preferably be masked such that all pixels beyond a boundary (for example below a noise threshold) are no longer considered. This has the advantage that regions of noise can be excluded from the following analysis because they cannot contribute to the decision as to which reference lines are to be used.

A preferred apparatus has a masking processor designed for masking the reference line images and/or the histograms thereof.

The histogram analysis is then carried out on the basis of the masked reference line images and/or the masked histograms.

Masking preferably proceeds in the image domain, preferably with threshold segmentation. Only pixels with a value above the threshold are here included in the mask. The histogram is determined from the pixels within the mask. Other types of segmentation, for example RegionGrowing or active outlines, are alternatively or additionally possible.

The reference line images are preferably the basis for masking.

Alternatively, the masking can proceed on the basis of associated Prescan Normalize data. Two images are acquired here, one with the body coil which is assumed to be homogeneous and one with the local coils which have strong receive profiles. A normalization correction for the actual acquisition may be calculated from the ratio. At the same time, however, a mask may also be calculated with the same segmentation as described above. The advantage is that the contrast levels and thus the threshold values change less strongly, very similar signal strengths above all being obtained in the body coil image.

The reference lines used for the PAT reconstruction are preferably those in which the pixels classified in the respective histogram have the highest signal strength. Particularly preferably, as described above, only pixels within the mask are considered.

The selection of those reference lines that are used for the PAT reconstruction is preferably dependent on the homogeneity of the signal distribution in the histogram and/or on the mathematical product of the number of pixels in the mask and the mean of the histogram.

The same reference lines are preferably used for the PAT reconstruction of all the contrast levels. Depending on the application, it is however also preferred to use different reference lines for PAT reconstruction of different contrast levels. Furthermore, mathematically combining the reference lines of both contrast levels, for example a mean of the reference line for the first and second contrast levels, is preferred.

Preferably, one line for calculating the GRAPPA kernel or one line for determining coil sensitivities for the purposes of SENSE is selected as the reference line.

BRIEF DESCRIPTION OF THE DRAWINGS

FIG. 5 shows histogram data masking.
FIG. 6 is a schematic illustration of a histogram analysis.
FIG. 7 schematically illustrates a magnetic resonance tomography system.

DESCRIPTION OF THE PREFERRED EMBODIMENTS

The following figures only include those elements that are essential to or of assistance in understanding the invention. Accordingly, no slice selection gradients, for example, are shown, although they may very well be present in the pulse sequence.

Figure 1:
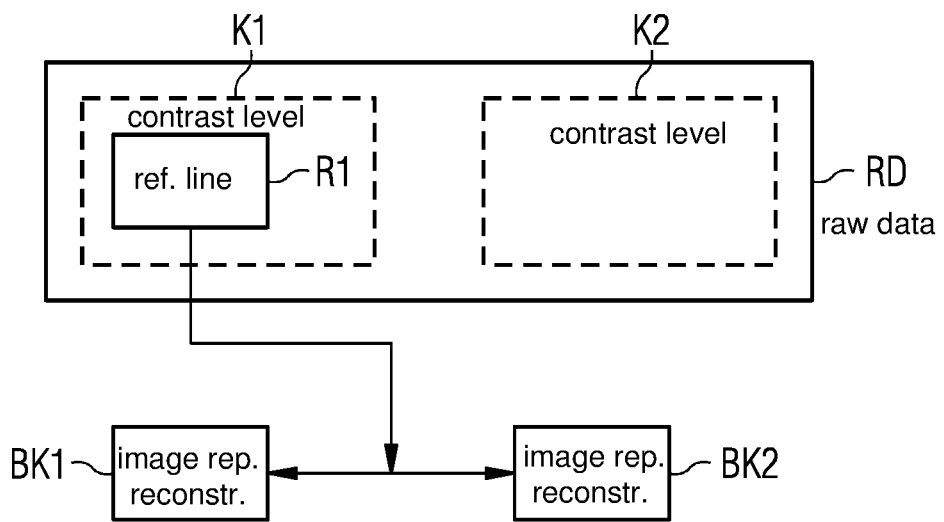
FIG. 1 schematically shows a method according to the prior art.

FIG. 1 schematically shows diagram of a method according to the prior art. Magnetic resonance raw data RD for at least two contrast levels K1, K2 are generated. This magnetic resonance raw data RD include reference lines R1.

These reference lines R1 are used for PAT reconstruction of image representations BK1, BK2 of the different contrast levels K1, K2.

Figure 2:
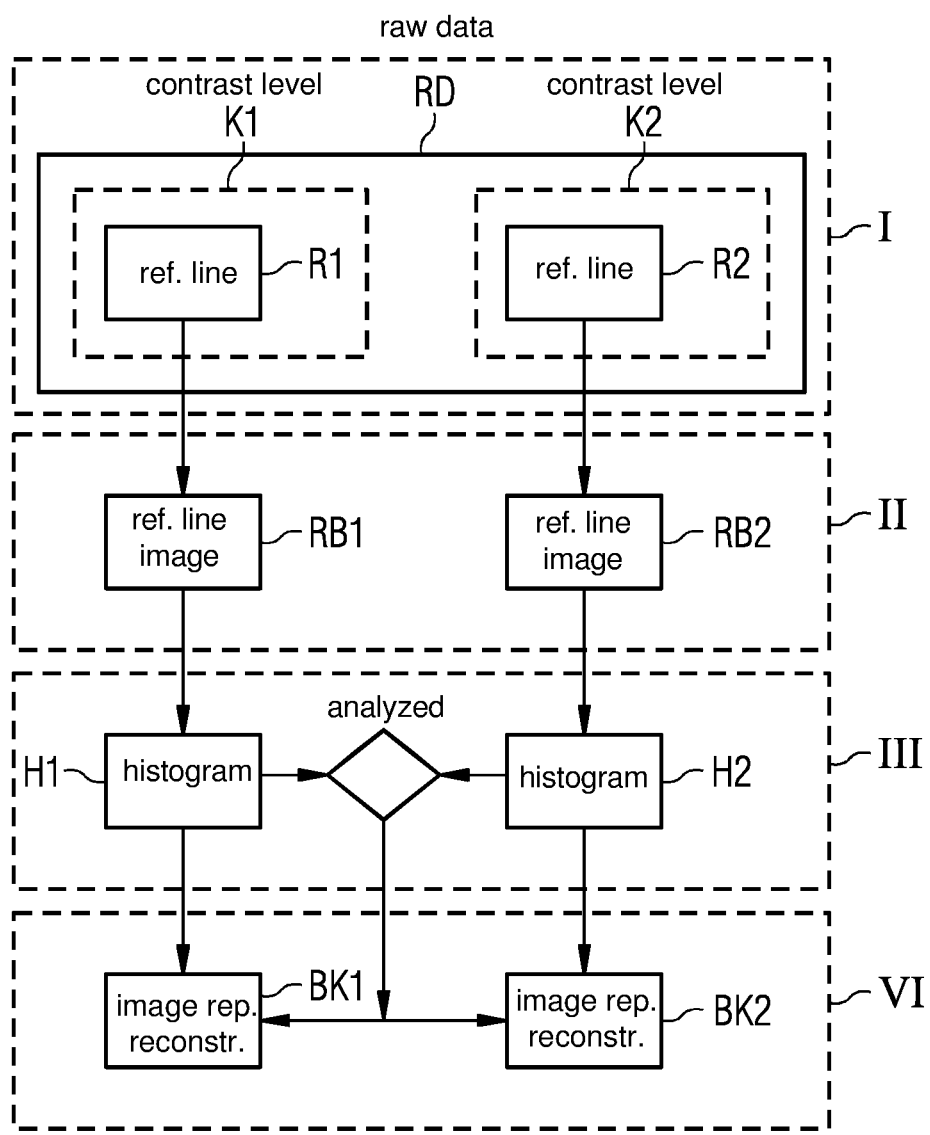
FIG. 2 schematically shows the method according to the invention.

FIG. 2 explains the method according to the invention for reconstructing contrast levels K1, K2 from magnetic resonance acquisitions.

In step I, magnetic resonance raw data RD for two contrast levels K1, K2 is provided (for example by PACS) or generated (by MRT). This magnetic resonance raw data RD here in this case comprises the acquisitions regarding contrast levels K1, K2 and reference lines R1, R2.

In step II, reference line images RB1, RB2 are reconstructed from reference lines R1, R2 (see FIG. 3) of the magnetic resonance raw data RD for both contrast levels K1, K2.

In step III, a histogram analysis proceeds on the basis of the reference line images RB1, RB2. To this end, a histogram H1, H2 (see FIG. 5) is generated for each reference line image RB1, RB2 and these histograms H1, H2 are analyzed (see FIG. 6).

In step IV, a PAT reconstruction of image representations BK1, BK2 of the two contrast levels K1, K2 is carried out, wherein the decision as to which reference lines R1, R2 are used for the PAT reconstruction is made on the basis of the histogram analysis.

Figure 3:
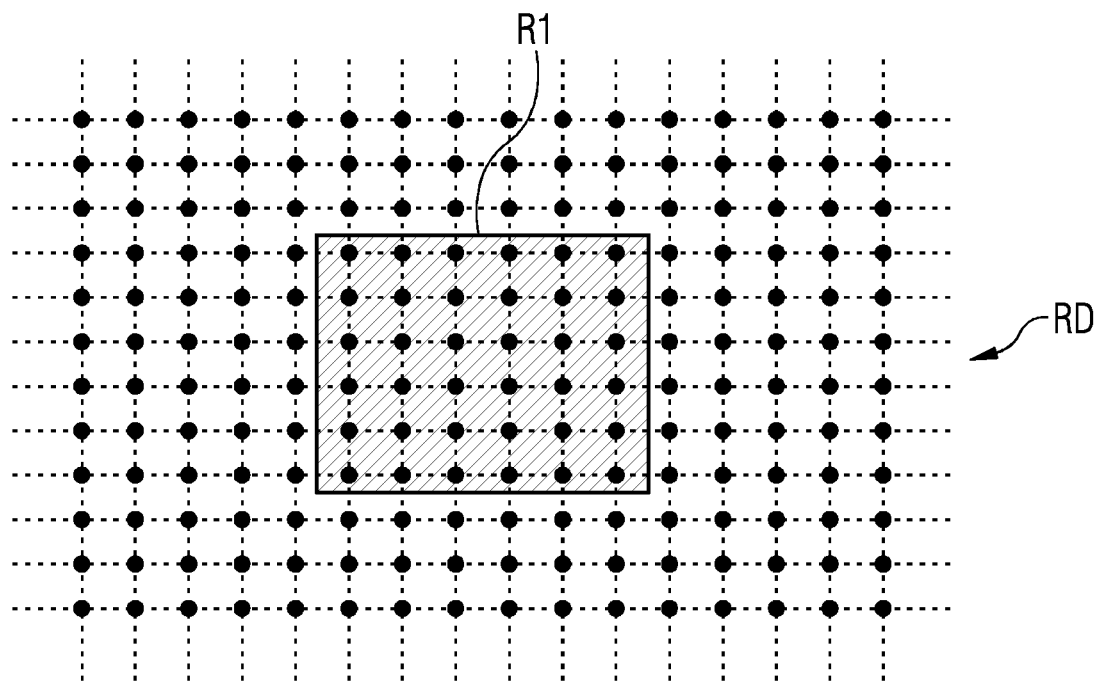
FIG. 3 shows reference lines in k-space.

FIG. 3 outlines reference lines R1 in k-space. The magnetic resonance raw data RD are here shown as a matrix of equidistant points in k-space. The reference lines R1 are now preferably taken from the center of k-space, as indicated by the crosshatched box. The points in the interior of this box are the reference lines preferably used in the method.

Figure 4:
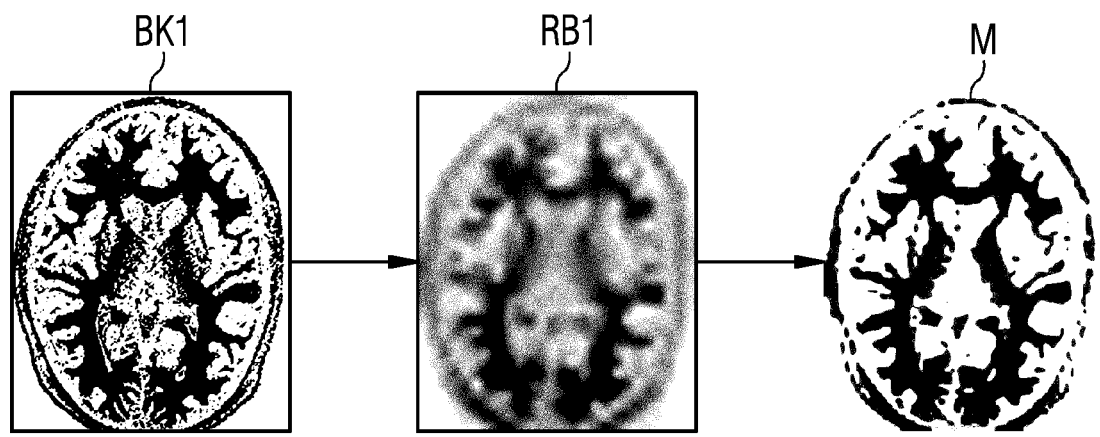
FIG. 4 shows image data masking.

FIG. 4 explains the principle of masking a reference image RB1 on the basis of a series of images. A contrast level is firstly acquired (here shown already as a reconstructed contrast level image KB1) which consists of a data set of magnetic resonance raw data RB and optionally other data. A subset of k-space data representing the reference lines R1 (see also FIG. 3) is formed from this raw data. A reference line image RB1, as shown here, is reconstructed from these reference lines. Since the reference line image RB1 does not comprise the entire raw data set of the contrast level, it is also not as detailed as the contrast level image KB1.

The reference line image RB1 is now masked such that the noise is excised. A mask M is obtained which comprises those pixels which are used for the histogram analysis.

Another kind of masking is, however, also possible.

FIG. 5 shows histogram data masking. A histogram is formed from a reference line image RB1, for example reference line image RB1 from FIG. 4, showing the value of a pixel on the x axis and the number of pixels with this value in reference line image RB1 on the y axis. In order to suppress noise, the left-hand part of histogram H1 may be cut off or only those pixels which are located within the mask M in histogram H1 may be considered. The entries in mask M in histogram H1 would also be obtained if reference line image RB1 had been correspondingly masked.

FIG. 6 shows a schematic diagram of a histogram analysis. Two histograms H1, H2 are here firstly formed from two reference line images RB1, RB2, as has been described above. The two histograms H1, H2 are masked as explained in FIG. 5 (either by masking reference line images RB1, RB2 or by directly masking histograms H1, H2) and only the inputs within the mask M are considered. Two masked histograms $H1_m$, $H2_m$ are obtained. It is now determined in in which of the masked histograms $H1_m$, $H2_m$ more pixels are present (in the case of histograms H1, H2 normalized prior to masking) or in which histogram H1, H2 the centroid is at a higher value. In the case shown, this is the upper masked histogram $H1_m$. The associated reference lines R1 are then selected by the method according to the invention in order to assist in reconstructing contrast level images KB1, KB2.

FIG. 7 is a diagrammatic representation of a magnetic resonance tomography apparatus 1. It includes the magnetic resonance scanner 2 with an investigation chamber 3 or patient tunnel, in which a patient or test subject, in whose body the actual object under investigation O is located, is positioned on a couch 8. Although in the example shown, the object under investigation O is depicted in the torso, diffusion tensor imaging is also often used for acquisitions of the brain, since it is particularly well suited to depicting neurological structures.

The magnetic resonance scanner 2 is, as is conventional, equipped with a basic field magnet 4, a gradient system 6, and an RF transmit antenna system 5 and an RF receive antenna system 7. In the exemplary embodiment shown, the RF transmit antenna system 5 is a whole body coil permanently installed in the magnetic resonance scanner 2, whereas the RF receive antenna system 7 is composed of local coils to be arranged on the patient or test subject (only indicated in FIG. 7 by an individual local coil). In principle, however, the whole body coil can also be used as the RF receive antenna system and the local coils as the RF transmit antenna system provided that these coils can in each case be switched to different operating modes. The basic field magnet 4 is here configured as is conventional such that it generates a basic magnetic field in the longitudinal direction of the patient, i.e. along the longitudinal axis extending in the z direction of the magnetic resonance scanner 2. As conventional, the gradient system 6 has individually drivable gradient coils in order to be able to switch gradients mutually independently in the x, y or z direction. The magnetic resonance scanner 2 additionally contains shim coils (not shown) which may be of conventional construction.

The magnetic resonance tomography system shown in FIG. 7 is a whole body system with a patient tunnel into which the entire patient can be introduced. In principle, however, the invention can also be used on other magnetic resonance tomography systems, for example with a C-shaped housing open at the side. All that is essential is that appropriate acquisitions of the object under investigation O can be prepared.

The magnetic resonance tomography apparatus 1 furthermore has a central control computer 13 that controls the MR apparatus 1. This central control computer 13 has a sequence controller 14. The latter controls the sequence of radiofrequency pulses (RF pulses) and of gradient pulses as a function of a selected pulse sequence PS or succession of a number of pulse sequences for acquiring a plurality of slices in a volume region of interest of the object under investigation within a measurement session. Such a pulse sequence PS may be predetermined and configured for example within a measurement or control protocol P. Various control protocols P for different measurements or measurement sessions are conventionally stored in a memory 19 and can be selected (and if need be optionally modified) by an operator and then used for carrying out the measurement. In the present case, the control computer 13 contains pulse sequences for acquiring the raw data.

In order to emit the individual RF pulses of a pulse sequence PS, the central controller has a radio-frequency transmit device 15, which generates and amplifies the RF pulses and feeds them into the RF transmit antenna system 5 via a suitable interface (not shown in detail). In order to switch the gradient pulses in coordinated manner with the predetermined pulse sequence PS, the control computer 13 has a gradient system interface 16 for controlling the gradient coils of the gradient system 6. The sequence controller 14 communicates suitably, for example by emitting sequence control data SD, with the radio-frequency transmit device 15 and the gradient system interface 16 for carrying out the pulse sequence PS.

The control computer 13 moreover has a radio-frequency receive device 17 (which likewise suitably communicates with the sequence controller 14) in order to receive in coordinated manner the magnetic resonance signals within the read-out window predetermined by the pulse sequence PS by the RF receive antenna system 7 and so acquire the raw data.

A reconstruction processor 18 here accepts the acquired raw data and reconstructs magnetic resonance-image data therefrom. This reconstruction processor 18 includes an apparatus 11 according to the invention (see FIG. 8), which is explained in greater detail below.

Those skilled in the art know how suitable raw data can be acquired by applying RF pulses and switching gradient pulses, and how MR images or parameter maps can be reconstructed therefrom, so a more detailed explanation is not necessary herein.

The central control computer 13 can be operated by a terminal with an input unit 10 and a display unit 9, via which the entire magnetic resonance tomography apparatus 1 may thus also be operated by an operator.

The magnetic resonance tomography apparatus 1 according to the invention and in particular the control computer 13 may furthermore also have a number of further components that are not individually shown here but are conventional in such systems, such as a network interface in order to connect the entire system to a network and enable exchange not only of raw data and/or image data or parameter maps but also of further data, such as patient-related data or control protocols.

Those skilled in the art are aware of a variety of measurement sequences, such as EPI measurement sequences or other measurement sequences for generating diffusion-weighted images.

Figure 8:
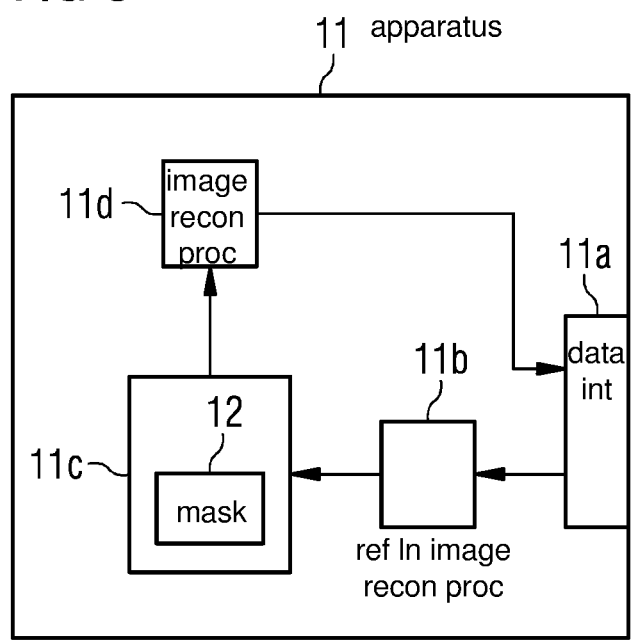
FIG. 8 shows an apparatus according to an exemplary embodiment of the invention in the form of a block diagram.

FIG. 8 shows a preferred exemplary embodiment of an apparatus 11 according to the invention in the form of a block diagram. This apparatus 11 enables the reconstruction processor 18 to provide advantageous image reconstruction and is preferably comprised by the reconstruction processor 18 but may also constitute a separate element, for example in the terminal.

The apparatus 11 has a data interface 11a for acquiring magnetic resonance raw data RD for at least two contrast levels K1, K2. In this example, reconstructed image data can also be transferred via the data interface 11a.

A reference line image reconstruction processor 11b designed for automatic reconstruction of reference line images RB1, RB2 from reference lines R1, R2 of the magnetic resonance raw data RD for at least two of the contrast levels K1, K2.

An analysis processor 11c which is designed for histogram analysis of the reference line images RB1, RB2. The analysis processor 11c here comprises a masking unit 12 which is designed for masking the reference line images RB1, RB2 and/or the histograms H1, H2 thereof.

An image reconstruction processor 11d which is designed for PAT reconstruction of image representations of the different contrast levels K1, K2, wherein the decision as to which reference lines are used for the PAT reconstruction is made on the basis of the histogram analysis. The image reconstruction processor 11d here transmits the reconstructed contrast level images back to the data interface 11a.

The method described above in detail and the depicted magnetic resonance tomography apparatus 1 are exemplary embodiments, which can be modified by those skilled in the art without departing from the scope of the invention Furthermore, use of the indefinite article "a" does not rule out the possibility of a plurality of the features in question also being present. Likewise, the terms "unit" and "module" do not rule out the possibility of the components in question consisting of a plurality of interacting sub-components which may optionally also be spatially distributed.

The invention claimed is:

1. A method for reconstructing contrast levels from magnetic resonance data acquired using a parallel acquisition technique (PAT), said method comprising:
   providing a computer with magnetic resonance raw data representing at least two contrast levels acquired from a subject, and said magnetic resonance raw data also comprising a plurality of reference lines;
   in said computer, reconstructing a plurality of reference line images respectively from said reference lines for at least two of the contrast levels among said at least two contrast levels;
   in said computer, conducting a histogram analysis of an attribute of the plurality of reference line images; and
   in said computer, implementing a PAT reconstruction of image representations of said at least two contrast levels in the magnetic resonance raw data, with selected reference lines, among said plurality of reference lines, being used in said PAT reconstruction dependent on an outcome of said histogram analysis.

2. A method as claimed in claim 1 comprising conducting said histogram analysis by producing an individual histogram for each of said reference line images that is calculated for at least two reference line images, and selecting said selected reference lines for use in said PAT reconstruction based on a signal strength of pixels classified in the histogram of the at least two reference lines.

3. A method as claimed in claim 1 comprising implementing said histogram analysis to identify a mean deviation and a standard deviation of a signal distribution in the respective line images, and using at least one of said deviation and said standard deviation of said signal distribution in order to select said selected reference lines for use in said PAT reconstruction.

4. A method as claimed in claim 1 comprising, before conducting said histogram analysis, masking, in said computer, at least one of said reference line images and said histograms using a mask, and conducting said histogram analysis based on at least one of the masked reference line images and the masked histograms.

5. A method as claimed in claim 4 comprising generating said mask based on associated Prescan Normalize data.

6. A method as claimed in claim 4 comprising conducting said histogram analysis to identify a homogeneity of a signal distribution in respective histograms, and selecting said selected lines dependent on said homogeneity of the signal distribution determined in said histogram analysis, or based on a mathematical product of a number of pixels in said mask and a mean of the respective histogram.

7. A method as claimed in claim 1 comprising conducting said histogram analysis to identify pixels classified in the respective histograms having a highest signal strength, and selecting said selected reference lines for use in said PAT reconstruction as a selected signal line having a highest signal strength.

8. A method as claimed in claim 1 comprising using same reference lines for said PAT reconstruction of all of said contrast levels, or using different reference lines for different contrast levels.

9. A method as claimed in claim 1 comprising using a selected reference line for at least one of calculating a GRAPPA kernel in said PAT reconstruction technique, or for determining coil sensitivities for a SENSE reconstruction in said PAT reconstruction technique.

10. A magnetic resonance (MR) apparatus comprising:
    an MR data acquisition scanner;
    a computer configured to operate the MR data acquisition scanner in order to acquire MR raw data representing at least two contrast levels acquired from a subject, and said MR raw data also comprising a plurality of reference lines;
    said computer being configured to reconstruct a plurality of reference line images respectively from said reference lines for at least two of the contrast levels among said at least two contrast levels;
    said computer being configured to conduct a histogram analysis of an attribute of the plurality of reference line images; and
    said computer being configured to implement a parallel acquisition technique (PAT) reconstruction of image representations of said at least two contrast levels in the MR raw data, with selected reference lines, among said plurality of reference lines, being used in said PAT reconstruction dependent on an outcome of said histogram analysis.

11. A non-transitory, computer-readable data storage medium encoded with programming instructions, said storage medium being loaded into a computer and said programming instructions causing said computer to:
    receive magnetic resonance raw data representing at least two contrast levels acquired from a subject, and said magnetic resonance raw data also comprising a plurality of reference lines;
    reconstruct a plurality of reference line images respectively from said reference lines for at least two of the contrast levels among said at least two contrast levels;
    conduct a histogram analysis of an attribute of the plurality of reference line images; and
    implement a parallel acquisition technique (PAT) reconstruction of image representations of said at least two contrast levels in the magnetic resonance raw data, with selected reference lines, among said plurality of reference lines, being used in said PAT reconstruction dependent on an outcome of said histogram analysis.

* * * * *